United States Patent [19]

Leader et al.

[11] Patent Number: 5,611,902
[45] Date of Patent: Mar. 18, 1997

[54] CATHODE IN A LAYERED CIRCUIT AND ELECTROCHEMICAL CELL FOR MEASUREMENT OF OXYGEN IN FLUIDS

[75] Inventors: Matthew J. Leader, Laguna Niguel; Jeffery A. Graves, San Juan Capistrano, both of Calif.

[73] Assignee: PPG Industries, Inc., Pittsburgh, Pa.

[21] Appl. No.: 355,423

[22] Filed: Dec. 13, 1994

Related U.S. Application Data

[60] Continuation of Ser. No. 106,504, Aug. 13, 1993, abandoned, which is a division of Ser. No. 624,948, Dec. 10, 1990, Pat. No. 5,246,576.

[51] Int. Cl.$^6$ .................................................. G01N 27/404
[52] U.S. Cl. .......................... 204/431; 204/400; 204/414; 204/415; 205/782; 205/783
[58] Field of Search ..................................... 204/400, 412, 204/415, 414, 429, 431

[56] References Cited

U.S. PATENT DOCUMENTS

| | | | |
|---|---|---|---|
| 2,913,386 | 11/1959 | Clark, Jr. | 204/195 |
| 3,000,805 | 9/1961 | Carritt et al. | 204/195 |
| 3,051,631 | 8/1962 | Harbin Jr. et al. | 204/195 |
| 3,098,813 | 7/1963 | Beebe et al. | 204/195 |
| 3,367,849 | 2/1968 | Blaedel et al. | 204/1 |
| 3,497,442 | 2/1970 | Vincent | 204/195 |
| 3,718,563 | 2/1973 | Krull et al. | 204/195 P |
| 3,835,013 | 9/1974 | Grubb et al. | 204/195 P |
| 3,997,420 | 12/1976 | Buzza | 204/415 |
| 4,021,326 | 5/1977 | Pollner et al. | 204/195 S |

(List continued on next page.)

FOREIGN PATENT DOCUMENTS

| | | |
|---|---|---|
| 0299778A3 | 1/1989 | European Pat. Off. . |
| 0309334A1 | 3/1989 | European Pat. Off. . |
| 0328640A1 | 8/1989 | European Pat. Off. . |
| 328640 | 8/1989 | European Pat. Off. . |
| WO91/08474 | 6/1991 | WIPO . |

OTHER PUBLICATIONS

"Laser Microfabrication and Activation of Graphite and Glassy Carbon Electrodes", *Analytical Chemistry*, K.D. Sternitzke, et al., Jul. 1990, vol. 62, No. 13, pp. 1339–1344.
"A Thick–Film Multiple Component Cathode Three–Electrode Oxygen Sensor", *IEEE Transaction On Biomedical Engineering*, by Vasilios Karagounis, et al. vol. BME–33, No. 2, Feb. 1986, pp. 108–112.

*Primary Examiner*—T. Tung
*Attorney, Agent, or Firm*—Kenneth J. Stachel

[57] ABSTRACT

The electrode of the present invention has metallic surface within a laser produced opening where the metallic surface extends into an electronic metallic conductive pathway and the pathway is covered for electric insulation by an encapsulant layer. The encapsulant layer around the metallic surface has the opening to allow the exposure of the metallic surface from the encapsulant layer. The metallic pathway and encapsulant are resident on a substrate, and are produced from layered circuitry. The electrochemical cell has the aforementioned electrode juxtaposed to another electrode. This electrode is part of the patterned metallic layer that is produced by layered circuitry. The electrode extends into an electronic metallic conductive pathway that is spaced apart and electronically insulated from the other pathway. The insulation can be supplied by a covering of encapsulant material that covers the pathway except does not cover the second electrode. The encapsulant would not cover the second electrode by virtue of its removal by laser and/or masking during production of the layered circuitry. Both of the electrodes are covered with an oxygen permeable fluid electrolyte that provides ionic contact between the two electrodes. The electrodes and electrolyte are covered with one or more oxygen permeable membranes, and these along with the metallic conductive pathways are resident on a substrate. The cell is useful in detecting oxygen in fluids when a negative potential is applied to the laser-produced electrode relative to the other electrode through the pathways that are in contact with leads for external electrical contact from the substrate.

8 Claims, 2 Drawing Sheets

U.S. PATENT DOCUMENTS

| | | | |
|---|---|---|---|
| 4,034,031 | 7/1977 | Lersmacher et al. | 264/25 |
| 4,041,440 | 8/1977 | Davis et al. | 338/195 |
| 4,076,596 | 2/1978 | Connery et al. | 204/1 T |
| 4,133,735 | 1/1979 | Afromowitz et al. | 204/195 G |
| 4,259,165 | 3/1981 | Miyake | 204/195 P |
| 4,269,685 | 5/1981 | Parker | 204/195 B |
| 4,298,573 | 11/1981 | Fujishiro | 422/94 |
| 4,410,785 | 10/1983 | Lilly, Jr. et al. | 219/121 LK |
| 4,450,065 | 5/1984 | Yamada et al. | 204/412 |
| 4,505,806 | 3/1985 | Yamada | 204/425 |
| 4,571,292 | 2/1986 | Liu et al. | 204/412 |
| 4,633,058 | 12/1986 | Jones | 219/121 LK |
| 4,638,110 | 1/1987 | Erbert | 136/246 |
| 4,781,798 | 11/1988 | Gough | 204/415 |
| 4,789,770 | 12/1988 | Kasner et al. | 219/121.7 |
| 4,795,542 | 1/1989 | Ross et al. | 204/415 |
| 4,851,088 | 7/1989 | Chandrasekhar | 204/1 T |
| 4,956,073 | 9/1990 | Pribat et al. | 204/426 |
| 4,980,043 | 12/1990 | Tomita et al. | 204/433 |
| 5,046,496 | 9/1991 | Betts et al. | 128/635 |
| 5,087,275 | 2/1992 | Pribat et al. | 55/386 |
| 5,246,576 | 9/1993 | Leader et al. | 204/415 |

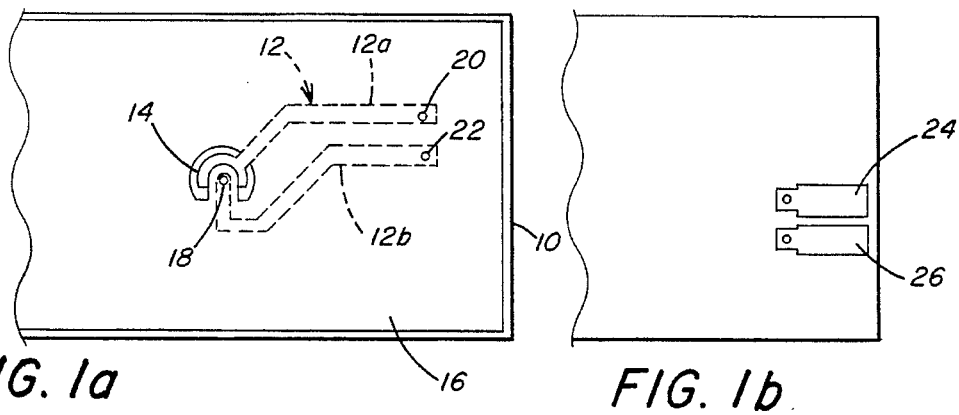
FIG. 1a
FIG. 1b
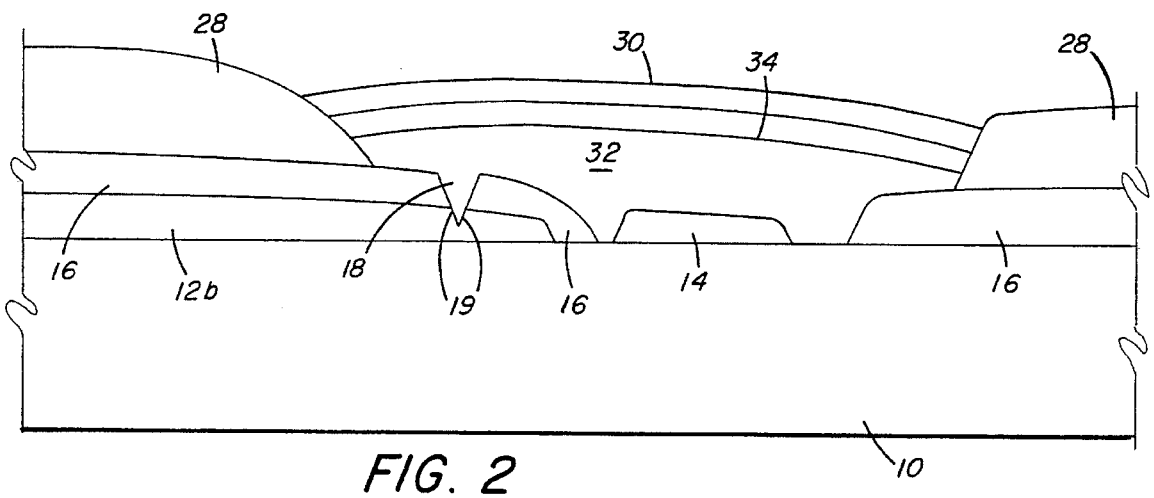
FIG. 2
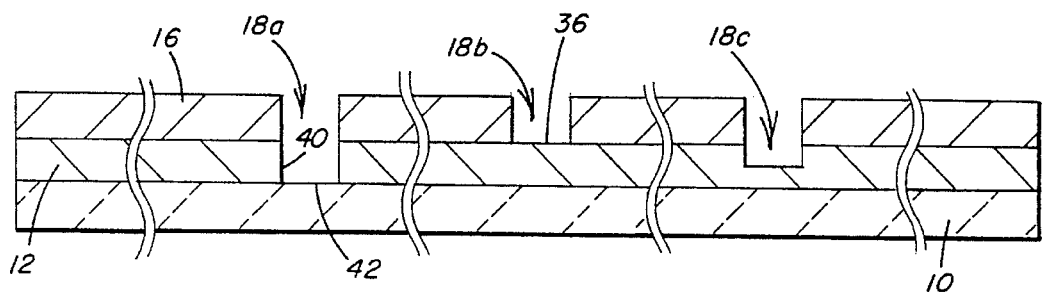
FIG. 3a
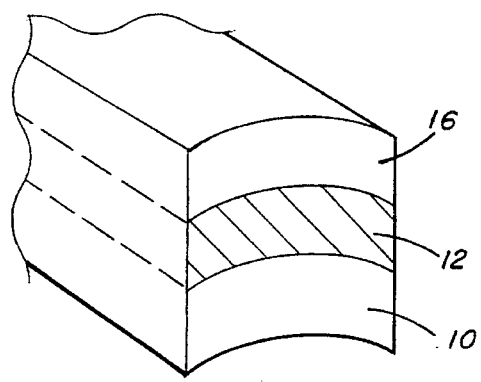
FIG. 3b

CATHODE IN A LAYERED CIRCUIT AND ELECTROCHEMICAL CELL FOR MEASUREMENT OF OXYGEN IN FLUIDS

This application is a continuation of application Ser. No. 07/106,504, filed Aug. 13, 1993, now abandoned, which is a division of application Ser. No. 07/624,948, filed Dec. 10, 1990, now U.S. Pat. No. 5,246,576, issued Sep. 21, 1993.

The present invention is related to the manufacture of a cathode in a layered circuit and electrochemical cells containing the cathode for use in sensors suitable for measuring oxygen in fluids. More particularly, the present invention relates to a cathode and the cathode in the electrochemical cell useful in a blood gas sensor having an improved measuring system for measuring the oxygen content of blood. Still more particularly, the present invention relates to an improved cathode of an oxygen measuring electrode assembly and a method for preparing it.

BACKGROUND OF THE INVENTION

The measurement of dissolved oxygen or oxygen-partial pressure or tension in fluids including gases and liquids is typically done with nonportable equipment utilizing electrodes for the oxygen measurement. This equipment is fairly expensive, and the procedures for its use can be cumbersome depending on the type of fluid to be measured. For instance, when the fluid is blood that is to be tested for blood gases, the blood sample is drawn in a syringe, immersed in ice and transported quickly to the lab where the equipment is usually located for a measurement of the gases including oxygen.

In these gas measuring machines the electrodes that are used to assist in sensing the oxygen normally consist of some configuration of the Clark cell or Clark electrode. The Clark cell normally consists of two electrodes, an anode and a cathode, both of which typically are formed by embedding a small wire, typically made of silver, gold or platinum into an insulating housing of glass or plastic to be used as the cathode and to surround the cathode with a ring or another wire typically made of silver to be used as the anode or reference electrode. The cathode and anode are in ionic contact typically by way of an ionic conducting electrolyte solution. The electrolyte is typically sealed into a chamber that holds the platinum wire and the reference electrode by means of a hydrophobic, gas permeable membrane that covers the whole assembly. This membrane serves two functions. It allows diffusion of the oxygen to the cathode surface. Also it provides a sensor with selectivity in restricting passage of materials which could possibly contaminate the cathode surface and interfere with the oxygen reduction reaction. The Clark electrode integrates the cathode and the reference electrode into a single unit. A voltage of about 0.5 to 0.8 volts is applied between the platinum wire and a reference electrode, which is also located in the electrolyte. With the platinum wire having a negative voltage with respect to the reference electrode, a reduction of the oxygen takes place at the platinum cathode. As a result, an oxidation-reduction current that is proportional to the partial pressure of the diffused oxygen is measurable. This current in a simple form is approximately $I=nFAf$, where n is equal to the number of electrons participating in the reduction, F is the Farady constant, A is the electrode surface area, and f is the oxygen flux to the electrode surface. These Clark electrodes assist in measuring gases like oxygen in fluids by their connection to the nonportable machines for the necessary electronics to obtain a read out of the value measured. They are placed in contact with the fluid to be measured, for instance blood, by placement in a cuvette of blood for in vitro measurement of the oxygen tension in the blood, or placement at the tip of a catheter for insertion into various parts of the body for in vivo measurements of oxygen tension in the blood.

Efforts have been made recently to provide more portable devices that shorten or overcome transporting the sample to the measuring machine at a fixed location. For example, portable sensing units which can be coupled to a digital readout device would be useful at the patient's bedside in a manner similar to a way that temperatures are measured at the patient bedside.

U.S. Pat. Nos. 3,000,805 and 3,497,442 show two such devices. The former has electrodes located on a syringe plunger and the latter has electrodes placed on the syringe well to conduct the measurements. The electrodes of these sensors may be particularly sensitive to small sample volumes since they consume oxygen in their operation. In the U.S. patent application Ser. No. 07/343,234, Applicants assignee describes and claims a portable blood gas sensor which includes an oxygen sensor fabricated using a conventional silk screening process where the electrodes are screened on to a ceramic substrate. The silk screening process, while effective in preparing electrical conductors, is limited in its ability to produce reproducible electrode surface area from batch to batch. The result is the production of sensors that give outputs that varies over a wide range even when the oxygen tension is a constant. Also, the large cathodes from the silk screening process consume amounts of oxygen in operation, and this degree of consumption makes stable measurements of small quantities of oxygen in the sample more difficult.

SUMMARY OF THE INVENTION

It is an object of the present invention to provide an improved cathode and an electrochemical cell with the cathode for use in an oxygen sensing device to detect the tension or partial pressure of oxygen in a fluid. The method of the present invention provides small, well defined cathodes that consume less oxygen than the cathodes produced from other processes such as silk screening. A uniform electrode surface area is provided, which allows for simplification in any electronics used for converting the electrical signals into a quantitative readout of the oxygen tension.

In one aspect of the present invention the improved cathode in a layered circuit has a multilayered composite of a nonconducting base, at least one patterned metallic layer disposed on the nonconducting base, and at least one encapsulant layer overlying all of the metallic layer but for at least one opening. The one or more openings are laser produced and extend from the top of the encapsulant layer overlying the metallic layer to at least the surface of the metallic layer or to any point into and including completely through the metallic layer in order to form an electrode. These one or more openings have a cross section that has a finite number of sides including circular and elliptical sides. The sides of the opening have at least the portion above the metallic layer composed of the encapsulant material such as glass, ceramics or a mixture thereof. The metallic surfaces within this opening defines an electrode that can function as a cathode in an electrode section of the metallic layer. The metallic layer is patterned to provide for the electrode section and a section that provides an insulated electronic conducting pathway for voltage and/or current between the electrode section and a distance remote from the electrode section.

The metallic layer is also patterned to allow for the capability of electrical connection from the nonconducting base by an electrical lead.

In another aspect of the present invention, the cathode is part of an improved electrochemical cell that can function as a sensor. The cell has a nonconducting base, at least one patterned metallic layer overlying the nonconducting base to define at least one distinct anode, at least one encapsulant layer that overlies the metallic layer except for an opening for the anode, and an oxygen permeable electrolyte. The nonconducting base comprises all or a part of the base for a printed wiring board that can be a planar board. In addition the patterned metallic layer has at least one laser produced opening that defines the aforementioned distinct electrode that can function as a cathode. Also the metallic layer has at least two insulated current paths that provide printed wiring from both the anode and the cathode to leads for each for external contact from the nonconducting base. The electrolyte is in ionic contact with both electrodes, where the laser produced electrode functions as the cathode and the other functions as an anode. In its broadest sense the cell has the anode and printed wiring formed by a layering technique and at least the cathode formed by a laser technique. Although it is within the scope of the invention to produce the electrode that functions as the anode by a laser production technique.

The method of the present invention involves applying to a nonconducting base a patterned layer of metal that is patterned for the presence of at least two distinct electrodes and wiring sufficient for electrical conduction from the electrodes to leads for external contact from the nonconducting base, covering the pattern layer of metal with an encapsulant layer in a manner at least sufficient to avoid exposure of the metal that needs to be electrically insulated. In another embodiment of the method, the encapsulant layer is applied in a manner to expose at least some of the metallic layer to form at least part of one of the electrodes. The application of metal and encapsulant may be a multilayered application so that each is at least one layer. The method also includes subjecting the resulting layered composite to a high energy laser beam to provide an opening in at least the encapsulant layer to result in a cathode. Where all or most of the metallic layer is covered with the encapsulant layer at least two openings are produced by the high energy laser to function as electrodes. The two openings in the encapsulant layer are spaced apart from each other but are sufficiently close for ionic contact through an oxygen permeable electrolyte. The laser is at a sufficient wavelength and beam power to vaporize a substantial thickness including at least the encapsulant layer. In addition, for improved stability of the electrochemical output, a predominant amount if not all of the chemically unstable residue (swarf) built up during the use of the laser beam may be removed. One convenient method of removing this material is through heating the layered composite after it has been subjected to at least one exposure to the laser beam where the heating is at a temperature above about 500° C. In this method, the encapsulant layer has a composition which is sensitive for vaporization at the particular wavelength of the laser. The laser can be used in the pulsed (blast) mode or the cut mode for producing the one or more openings that function as electrodes.

BRIEF DESCRIPTION OF THE DRAWINGS

FIG. 1a is a top planar view of one side of the electrochemical cell of the present invention, where the electrodes are located, and FIG. 1b is a planar view of the other side of the electrochemical cell of the present invention that has the leads connected through the board from the first side to provide an external electrical connection from the board.

FIG. 2 is a cross sectional view alone lines I—I of FIG. 1a and rotated 90 degrees.

FIG. 3a shows three possible variations of a cross sectional view of the cathode of the electrochemical cell where the cross sections is similar to that of FIG. 2 and where the openings have been enlarged for clarification.

FIG. 3b is a perspective view of a cross section through FIG. 3a on a 45° angle or alone lines II—II and where the opening extends into the ceramic board.

DETAILED DESCRIPTION OF THE INVENTION

Figure 4:
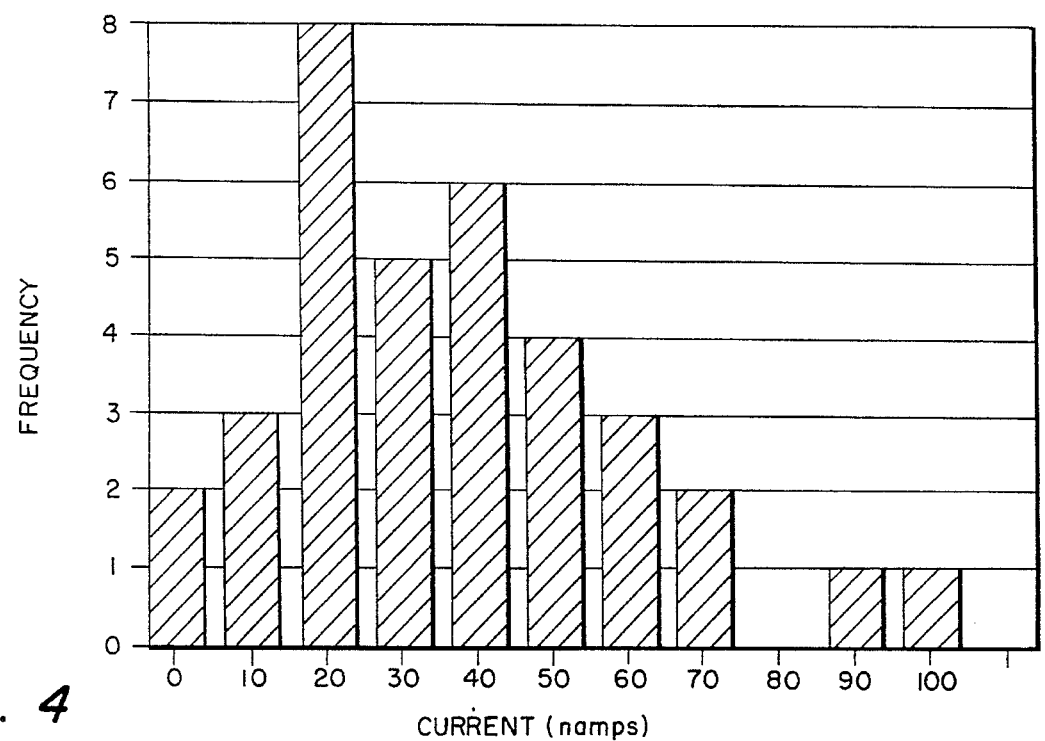
FIG. 4 is a bar chart of the electrochemical cell output current alone the abscissa versus the frequency alone the ordinate for electrodes produced by screen printing technology. This shows the distribution of current representing a group of electrodes formed by this method.

In producing an electrochemical cell from known layered circuit technology for use in measuring oxygen in a fluid, the cathode tends to be on the order of around 0.007 to 0.013 inches in diameter. The use of these cells in measuring oxygen in fluids can produce currents over a wide spread from a few nanoamps up to hundreds of nanoamps. This size limitation of the cathode occurs whether the hybrid layered circuitry is produced through thick film, thin film, plating, pressurized laminating, photolithographic etching or general etching technology.

The cathode and the electrochemical cell having the cathode of the present invention provide more uniformity from cathode to cathode and smaller cathode surface area to narrow the range of the output current and also to reduce the amount of oxygen in the sample that is consumed by the cathode. The present invention achieves these benefits by utilizing layered circuitry with laser drilling to produce at least one electrode for an electrochemical cell useful in oxygen measurement. The laser drilling produces both a smaller cathode surface area and reproducibility of the cathode surface area from lot to lot. An additional benefit is the capability of using a linear current output from the cathode. The present invention allows for less complex electronics for use in measuring small to minute quantities of oxygen in small sample sizes of fluids. This is true for any screening process that is employed for producing the layered circuit. The cathode current produced from the cathode and electrochemical cell of the present invention can have a narrow range from 1 to around 10 nanoamps. This range is comparable with that achieved in bulkier more complex electronic instrumentation for sensing oxygen in fluids. With such lower output currents, there is minimal depletion of the oxygen concentration in sample sizes as small as those having volumes from 100 to 500 microliters.

FIG. 1a shows the preferred embodiment of the electrochemical cell of the present invention where the components have particular shapes. Any other shapes than those shown in FIG. 1a that are known to those skilled in the art for the particular components can also be used. The cell is produced from any one of the aforementioned layered circuit technologies, but the thick film technique is preferred. In both FIGS. 1a and 1b, a substrate 10 is any glass or ceramic including sheet or chip or nonconducting substrate like wood or nonconducting polymers or commercially available frit that can be used as the substantially smooth flat surface of the substrate. Nonexclusive examples include: borosilicate glass as is known to those skilled in the art for producing thick film or layered circuits. A nonexclusive but preferred example of which includes a ceramic base having around 96 percent $Al_2O_3$ such as that available commercially from Coors Ceramic Company, Grand Junction, Colo. The substrate is essentially flat and any substrate known to those skilled in the art useful for forming printed wiring circuits can be used. It is preferred that the composition of the substrate can endure the presence of electrolyte that has a pH in or over the range of 6 to 9 and remain unaffected for a substantial period of time.

On the substrate layer is a patterned metallic layer 12 having two extensions 12a and 12b to act as electronic conducting pathways between a voltage or current source external to the cell (not shown in FIGS. 1a and 1b) and each of two separate electrodes. The extensions constitute the transmission section, where each extension has an electrode at similar ends. One electrode is located at one end of one extension (a) and the other electrode is located at a similar end of the other extension (b). Extensions 12 (a) and (b) also have the ability to transmit changes in voltage from the electrodes to a metering device, which is not shown in FIGS. 1(a) or (b). Also the patterned metallic layer has metallic external leads 24 and 26 as shown in FIG. 1(b) on the other side of the substrate 10. Although the external leads 24 and 26 are shown on the opposite surface of substrate 10, they can also be on the same surface as the metallic lead patterns and electrodes. The patterned metallic layer is formed by printing pastes deposited onto a substrate in the desired pattern to act as ohmic conductors. Nonexclusive examples of suitable heat resisting metals include: noble metals such as platinum (Pt), ruthenium (Ru), palladium (Pd), rhodium (Rh), iridium (Ir), gold (Au), or silver (Ag) or other metals traditionally used in Clark cells. A nonexclusive but preferred example of a suitable paste is a silver paste of the type produced and available from Electro-Science Laboratories, Inc. under the trade designation ESL 9912. At the one end of one of the extensions, here extension 12(a), electrode 14 is patterned to function as an anode. The shape of the anode can be any known to those skilled in the art but preferably is a semi-circular shape to ensure uniform current density between the anode and cathode electrodes. The shape of the anode can be any shape known to those skilled in the art to allow for ionic relationship between the electrodes through an electrolyte. If multiple layers of encapsulant and metallic conductive layers are present, the anode can also be in the shape that completely surrounds the cathode. Also the anode may be located on the opposite side of the substrate as the cathode, if a thru hole is provided as a common path for ionic migration.

The metallic layer 12 is dried to produce the patterned conductive pathways 12a and 12b of FIG. 1(a) and external leads 24 and 26 of FIG. 1(b). Any method known to those skilled in the art for producing a sufficient thickness of the metallic tracing can be used. Preferably, the silver pastes are oven dried and fired at a high temperature in a furnace. Firing can be accomplished at a temperature in the range of around 800° C. to 950° C. for time around 1 to 20 minutes. With this procedure, the thickness of the layer of the metallic conductive tracing is usually in the range of around 0.0005 to 0.001 inches. Although the afore-mentioned are preferred conditions, general conditions for obtaining a proper thickness can be used where the thickness can generally range from about 0.0004 to 0.0015 inches.

The metallic conductive patterns 12a and 12b are encapsulated with a glass or glass ceramic mixture or a ceramic insulating material such as alumina or spinel. This encapsulation can range from total encapsulation to encapsulation except at the shaped end of the one metallic pattern. In the former circumstance, the shapes of both of the electrodes would be produced by a laser as is subsequently described for the production of one of the electrodes that can act as the cathode. In FIG. 1a, the shaped end 14 that can function as the anode is preferably produced by one of the layered circuit techniques. This involves leaving the shaped end 14 uncovered while metallic patterns 12a and 12b are completely covered by the encapsulant. The encapsulation of the metallic patterns can range from encapsulating each from the other to a sufficient degree for electrical insulation of the conductive patterns and any conductive layers from each other. Also as shown in FIGS. 1a and 1b the encapsulant can extend across the whole board from edge to edge as generally shown at numeral 16. Preferably, the thickness of the encapsulant layer is that which is adequate to seal the underlaying metallic conducting layer and to provide insulation for the metallic patterns. Preferably, the thickness of the layer is around 20 to 30 microns. A preferred glass ceramic mixture useful as the encapsulant is that available from Electro-Science Laboratories, Inc. under the trade designation ESL 4903. When the encapsulant does not cover anode 14 this can be accomplished by a process of masking. This process involves masking of the anode by the use of a polymer film coating on the screen used to screen print the encapsulant. This leaves the underlying silver exposed to form the shape or geometry of the anode. It is also possible to use multiple layers of the metallic conductive layer or encapsulant to assure that little, if any, metal other than possibly the anode is exposed prior to formation of the cathode. Preferably, the glass composition for the encapsulant as with the composition for the substrate 10 is selected to possess good chemical stability and/or moisture resistance. Also, the metallic and encapsulant materials are selected so that they can endure the presence of an electrolyte in a similar manner as the substrate composition.

In at least one of the metal patterns and as is shown in FIG. 1(a) at 12b at least one opening 18 is laser produced. The opening can be of any shape, elliptical, elongated, cylindrical, conical, and extends at least through the encapsulant layer to expose at least the top metallic surface. This surface is the surface of the metallic conductive layer that is closest to the encapsulant layer. The location of the laser drilled cathode to the printed formed anode is that which allows for ionic contact when a fluid electrolyte covers both the cathode and the anode 18 and 14. Preferably, the distance from the center of the cathode to the edge of the anode is in the range of around 0.013 to 0.015 of an inch.

Opening 18 can be produced by a laser beam that is coherent radiation produced as a high-powered focused pulse or series of pulses of electromagnetic energy directed to the surface of the ohmic conductor 12b at the end close to electrode 14. The wavelength of the laser beam is that which is sufficient to be absorbed by the encapsulant. Examples of such wavelengths are 1064 nanometers (infrared) to about 532 nanometers (green). This optical radiation is concentrated in a small spot size and with sufficient power vaporizes or sublimates the material on the composite substrate on contact to leave a cavity or opening of controlled diameter and depth. The laser can be a short wavelength laser such as a neodymium-doped-yttrium-aluminum garnet gas laser (Nd-YAG) or any other type of short wavelength laser. A suitable nonexclusive example of such a Nd:YAG laser is that described in "Biomedical Instrumentation and Technology", pages 10–18 and the "CLS Laser Trim System User's Manual" from the Chicago Laser Systems, 4034 North Nashville Avenue, Chicago, Ill. A longer wavelength laser such as the $CO_2$ laser or dye laser could also be used with the proper beam-absorbing composition used for the encapsulant layer. The advantage of the pulsed laser beam is that the beam size power density and pulse frequency are controllable. Preferably, one or more pulses are used to form at least one cylindrical conical hole for opening 18 and the pulse standard rate is preferably between about 4 to about 15 pulses in about 100 milliseconds. The preferred laser used is the standard CLS Model 37S laser operating in a blast mode at a Q-rate (pulse frequency) of about 4,000 to 10,000 hertz to deliver a laser beam having a power of around 0.6 to 2.0 watts and having around 4 to 15 pulses per hole. These conditions can very somewhat and still produce an acceptable opening 18 with surrounding structure. It is also possible to have other shapes for opening 18, where the laser beam moves to carve out a shape. Preferably, the size of the finite-sided opening 18 is sufficient in depth to allow the opening to extend through the thickness of the encapsulant layer, but minimal in diameter to reduce oxygen consumption during measurement. It is preferred to have the surface of the cathode as small as possible to consume lesser amounts of oxygen from the sample fluid when measuring the concentration of oxygen in the fluid. If greater thicknesses of the encapsulant layer are used, then a concomitant increase in the pulses is used to produce opening 18 extending through the encapsulant layer 16.

In general, opening 18 is produced by the focused laser beam drilling a hole by heating a small volume of material to a sufficiently high temperature for localized melting and/or vaporization. The characteristics of the drilled hole would depend on a number of factors, including a laser beam power and pulse parameters, the laser wavelength, and the reflectance, composition, strength and heat transfer properties of the encapsulant material. The use of a Nd-YAG laser will produce a beam that is more readily absorbed by the metal surface thereby producing an opening 18 that extends into the metal. Longer wavelength lasers, such as the $CO_2$ laser, also produce a beam that is readily absorbed by the encapsulant material.

In addition, the laser is used to drill holes 20 and 22 in the substrate at the locations of metallic patterns 12a and 12b respectively. The purpose of this drilling is to conductively connect the metallic traces 12a and 12b on one side of the ceramic board 10 with metallic external leads 24 and 26. External leads 24 and 26 are shown in FIG. 1(b) on the second side of the substrate 10 opposite the first side where the electrodes are located. These external metallic leads can be produced on said other side of substrate 10 with the same paste and firing as that done for metallic patterns 12a and 12b. The external leads of FIG. 1(b) (24 and 26) are in metallic electrical conducting contact with the lead wire layers of metallic patterns 12a and 12b on the second side of the substrate 10. The holes 20 and 22 have been drilled through the substrate and when the metallic layers are screened such electrical connections are formed. Alternatively, the metallic external leads can be produced and preferably are produced by a very high powered carbon dioxide laser. This can be accomplished by the supplier of the nonconducting substrate and in this case the metallic layer is added to the substrate so each electrical conducting pathway electrically connects with an external lead.

As an alternative, the electrode that acts as the anode can be laser produced in a similar manner to the electrode that acts as the cathode rather than forming this electrode by layered circuitry techniques. In this alternative the shape or geometry of the electrode could be made by moving the laser beam of the work piece to cut or carve or trim the electrode. The larger the size and shape of the electrode the more costly it would be to produce it through laser production. Hence, larger sized electrodes, are preferably prepared through the layered circuit technique.

As shown in FIG. 1(a) the electrode within opening 18 with the conductive path 12(b) and with conductive connection 22 to external lead 26 can act as an electrode in any printed wiring board arrangement. For example, it can function as a cathode for any electrode that acts as the anode. The electrode of the present invention could be used as the cathode in conventional Clark Cell arrangements in current commercially available nonportable blood gas analysis equipment.

FIG. 2 is a view of the cross section through lines I—I of FIG. 1(a). Here the substrate 10 is shown as a cross section having the metallic ohmic layer 12b covered by the encapsulant layer 16. Layer 16 also insulates the opening 18 from anode 14 which is also the metallic ohmic layer that will be attached to conducting wire 12a not shown in FIG. 2. The encapsulant layer 15 insulates the anode 14 on its other side. The cross section of the electrochemical cell depicted in FIG. 2 has at least one encapsulant layer. The thickness of the encapsulant layer ranges as mentioned before in micrometers of thickness. Competing factors for the thickness of the encapsulant layer are that the thicker the layer the more laser drilling is required to uncover the metallic surface for opening 18 but that the thickness must be sufficient to allow for other components of the electrochemical cell. For this reason, it is preferred to have two encapsulant layers, the first being layer 16 and second being layer 28. Layer 28 would not completely overlap layer 16 in the vicinity of the anode 14 to allow for laser drilling of the uncovered encapsulant layer 16. This would allow for a thinner layer of encapsulant to be laser drilled while still providing the proper thickness of the encapsulant layer for other components to be added to the electrochemical cell. The electrode 19 of FIG. 2 is the surface of the metallic layer that comprises the wall encompassing opening 18. This electrode merges into the metallic layer 12(b) shown in FIG. 1(a).

One of these other components is at least one oxygen permeable membrane 30 which allows oxygen to enter the electrochemical cell but does not allow the fluid electrolyte 32 to leave the cell. The membrane 30 is commonly referred to as a hydrophobic membrane. The membrane is designed to reduce poisoning of the cathode by selective permeability for oxygen so non oxygen species other than the fluid electrolyte 32 are blocked from access to the electrode. In addition to protecting the electrodes, the oxygen permeability of the membrane creates a diffusion limiting flux of oxygen to the surface of the cathode. The membrane 30 can be produced from polymeric materials such as polystyrene in an organic or inorganic solvent. Other suitable examples include high molecular weight polyvinyl chloride or silicone rubber, polypropylene or polyethylene. When the solution is applied as a droplet, it is dried by solvent evaporation to achieve a controlled thickness in the range of around $1 \times 10^{-3}$ to around $3 \times 10^{-3}$ inch. It is also possible to have more than one membrane present that is oxygen permeable. A nonexclusive example of a membrane 30 is polystyrene deposited from 10 milliliters of xylene. The submembrane 34 would be formed first in a manner similar to that described for the formation of the membrane 30. After formation of membrane 34, membrane 30 would be subsequently formed.

Fluid electrolyte 32, which is oxygen permeable, bathes the anode 14 and cathode opening 18 to provide electrical ionic contact between the two. The electrolyte can be any electrolyte known to those skilled in the art for Clark cells. A nonexclusive example is saline solutions based on potassium chloride or sodium chloride. Other suitable electrolytes are described in the reference entitled "Measurement of Oxygen Membrane Covered Probes", Linek, You et al, Horwood, Ltd., 1988, which is hereby incorporated by reference. Preferably, the electrolyte 32 is a fluid which includes a liquid and a gel. The electrolyte is preferably placed in contact with the electrodes before formation of the one or more membranes over the electrodes and electrolyte. A nonexclusive example of the liquid electrolyte is potassium chloride in a buffered solution such as one having 0.1 mole potassium hypophosphite ($K_2HPO_3$).

FIGS. 3a and 3b show variations on the opening of the cathode electrode 18. In FIG. 3a the substrate 10 which is usually around 0.020 to 0.025 inch thick forms the base. Opening 18a extends down through the encapsulant layer 16 and through the metallic layer 12. The electrode in opening 18a is actually an annular ring formed in the metallic layer 12 by the opening. Opening 18b merely extends through the encapsulant layer 16 and stops at the top surface of the metallic layer 36. Here the top surface 36 is the electrode and this is the preferred electrode to act as the cathode. Opening 18c depicts another variation of the opening size extending through all of layer 16 and some portion of the metallic layer 12. In this embodiment the electrode is an annular ring a portion of which is shown at 40 that is formed in metallic layer 12 by the opening and the nearly flat or at least somewhat horizontal surface 42 at the bottom of the opening. The opening for the cathode of the present invention can encompass all of these variations from laser drilled cathode to laser drilled cathode in various lots. FIG. 3b is a perspective view of a cross section of opening 18 showing a section of the annular ring of 40 that can act as all or part of the electrode. The opening extends through all three layers, 16 for the encapsulant, 12 for metallic layer, and 10 for the substrate. In this situation, a bottom surface must be placed on opening 18. Suitable examples of such surfaces include a polymeric membrane surface similar to that of the membrane 30 or 34.

The two electrodes 19 and 14 of FIG. 2 operate to sense oxygen in a manner similar to that for a conventional Clark Cell. The electrodes are polarized relative to one another at a fixed potential usually by application of a voltage of preferably around 0.5 to around 0.8 volts. Preferably, cathode 19 of FIG. 2 is held at a negative potential with respect to the anode 14 typically in the range of −500 to −800 millivolts. In the electrochemical cell of the present invention this potential can be applied through the external leads 24 and 26 to the electrodes through conductive pathways 12(a) and 12(b). The oxygen permeates the one or more membranes 30 and 34 and permeates the electrolyte 32 and is reduced at the surface of electrode 19. The reduction results in the production of a current flow. As with the Clark cell, this current is a function of the oxygen pressure in the measuring fluid. The current is approximately equal to the number of electrons participating in the reduction multiplied by the Faraday constant multiplied by the electrode area surface multiplied by the oxygen flux to the electrode surface. The current flow is transmitted through the conductive pathways 12(a) and 12(b).

The oxygen permeates the one or more membranes 30 when the electrochemical cell is brought in contact with a fluid having an oxygen tension or dissolved oxygen. The term "fluid" depicts any liquid having dissolved oxygen where the liquid can also have other dissolved gases and also suspended solid and/or gelatinous materials. An example of a fluid for which the electrochemical cell can be used to measure the oxygen concentration is blood. It is preferred in measuring the oxygen concentration of blood by the partial pressure of oxygen that the cathode has a diameter between around $1 \times 10^{-3}$ to $1.5 \times 10^{-3}$ inch. This typically takes 15 pulses of an Nd-YAG laser at a beam power of 2 watts on an encapsulant layer having the aforementioned preferred thickness to produce a cathode having a tapered opening similar to that of FIG. 2 but that only extends to the top surface of the metallic layer as shown at 18b of FIG. 3a. With this configuration, the cathode size is well defined because the thickness of the metallic ohmic conductor can be controlled very accurately with the thick film process and the size of the hole can be controlled very accurately with the laser. Also, an additional advantage is that the cathode is inside the laser drilled hole thus restricting oxygen diffusion to the cathode surface by a linear process which eliminates non-linear complications which may arise because of any side diffusion of oxygen to the cathode surface. In other words the flux of oxygen to the cathode surface becomes well defined.

Figure 5:
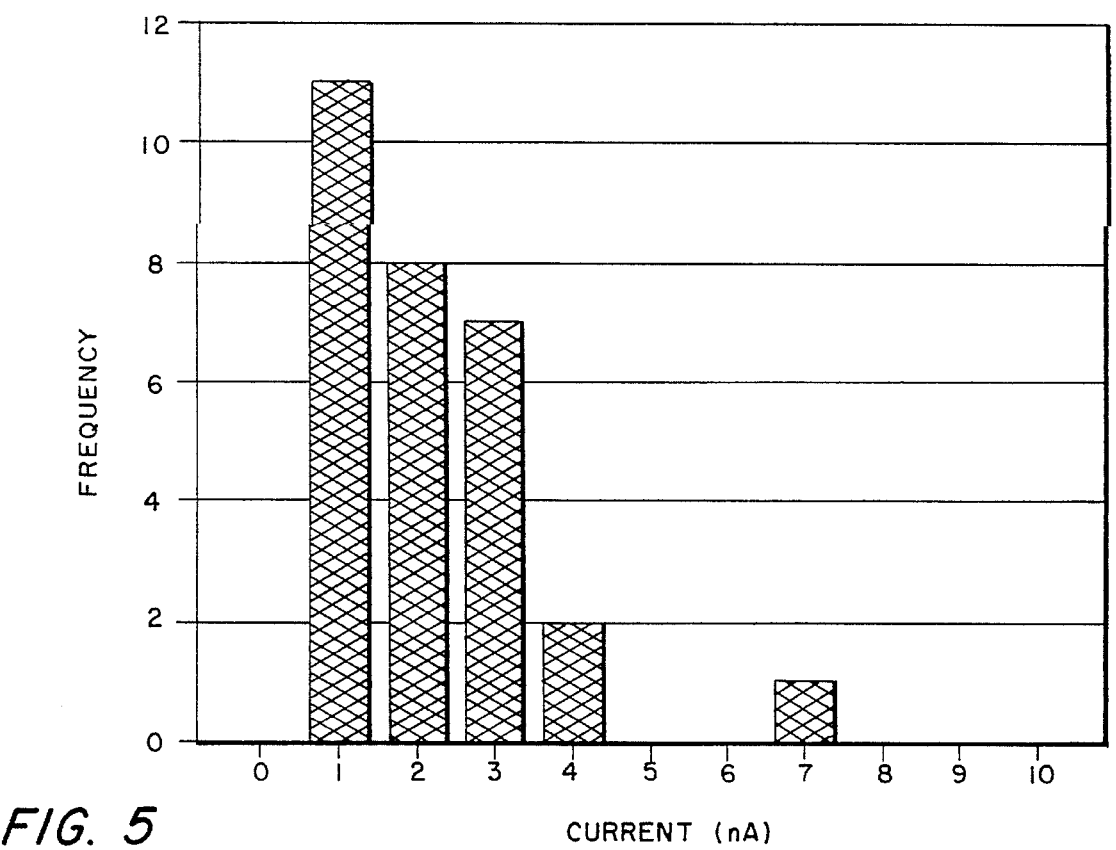
FIG. 5 is a bar chart of the same current on the abscissa versus the frequency on the ordinate for electrodes of a group of electrochemical cells produced by the present invention showing the current distribution.

FIGS. 4 and 5 show a comparison of the current in nanoamps produced over a number of cathodes produced by a thick film process as shown in FIG. 4 and the laser drilled cathode of the present invention shown in FIG. 5. For a number of thick film electrodes, the current ranges from close to 0 all the way up to 100's of nanoamps giving a broad distribution of currents. FIG. 5 shows that the laser drilled cathode in the present invention produced a much narrower band of current output in measuring the oxygen concentration in fluids.

Prior to any measuring of oxygen concentration the electrochemical cell may be stored with exposure to a liquid solution such as 0.1 molar potassium chloride in a pH 7.4 buffer. To measure the oxygen concentration of a fluid, the electrical chemical cell is brought in contact with the volume of fluid to be measured. This volume of fluid can be quite small ranging from as small as a few microliters and having very low oxygen tensions. To determine the oxygen tension of the fluid, the current which is produced from the reduction of oxygen at the cathode is electrically conveyed along wire pattern 12b of FIG. 1 to the external lead 26. The external leads are then connected to an analog or digital display to display the current produced. Electrochemical cell can be used with a suitable electronics module for the appropriate electronics to convert directly to a reading for the amount of oxygen in the fluid; otherwise, having a digital display of the current requires the performance of calculations to arrive at the oxygen concentration. In addition, the electrochemical cell can be connected to any electronics utilized with traditional Clark cells to display the oxygen concentration with appropriate modifications to the electronics known to those skilled in the art to provide necessary polarization voltage and necessary signal processing for converting the signal current to a known oxygen tension.

The method of producing the electrochemical cell and the cathode of the present invention allows for the production of reproducible and interchangeable electrochemical cells for oxygen sensors. It is believed that the laser beam vaporizes the glass coating over the metal layering thereby creating the cavity 18. During this process, a variety of non-stoichiometric compounds and reduced oxide glass phases are residual in the locale of the cathode. After laser drilling, the method preferably includes heat treating the laser drilled composite substrate to convert these metastable species (swarf) to more stable phases preferred to assure long-term stability of the electrochemical cell.

The method of preparing the electrode and the electrochemical cell of the present invention utilizes the layered circuit technique.

The heat-resistant metal having ohmic conducting properties is applied as a patterned layer of to a nonconducting substrate. The pattern has a transmission section having at least one electronic conductive pathway with two ends spaced apart from each other but connected together so that generally the length is greater than the width. The metallic layer is fired to produce the patterns that preferably have a thickness in the range of around 0.0005 to 0.0015 inch. This process step is more fully described in the previous description for FIGS. 1, 2 and 3.

An encapsulant layer is applied over the surface of the metallic pattern ranging to totally encapsulate the pattern that will have the laser-produced electrode. To produce the electrochemical cell the metallic pattern can be totally encapsulated where two electrodes will be present. In this case the small sized electrode which usually acts as the cathode and the other electrode that can act as the anode are laser produced. Alternatively the larger electrode can be at least partially produced by the layered circuit technique so that some part of the metallic pattern in proximity to where the smaller electrode will be located is uncovered by the encapsulant layer. In this case any additional encapsulant material that must be removed to produce an electrode can be removed by the laser. Preferably, the larger electrode is uncovered by the encapsulant layer. This is accomplished by masking the metallic layer to form a shape of an anode. The encapsulant coated metal pattern layer on the substrate is dried and fired or sintered at a temperature in the range of 500° C. to 950° C. to form an encapsulant layer that electrically insulates individual metallic patterns one from the other. Preferably, the thickness of the layer is around 20 to 30 microns thick.

The method utilizes a high energy pulsed laser beam in the aforementioned manner. Generally, the laser blasts an opening in at least one layer of encapsulant insulating material at the end of the totally encapsulated metallic pattern that is in the vicinity of the anode. Generally, the diameter is not greater than around 0.0018 inch and the hole extending at least through the encapsulant layer. Generally, the ratio of the surface area of the anode to the surface area of the cathode is at least 50 to 1. After formation of the laser drilled opening to form the cathode, the layered material is heat treated once again at a temperature of above about 500° C. to remove all of the swarf on the walls of the laser drilled hole to thereby complete the cathode. Preferably, the temperature of the final heat treating step is in the range of between 525° C. to 650° C.

The electrochemical cell is produced by having present the larger electrode in addition to the smaller electrode in the metallic pattern and having present fluid electrolyte in contact with the two electrodes. Also the two electrodes, cathode and anode, and fluid electrolyte are covered with one or more (and preferably one) oxygen permeable membranes. These are formed in the fore-described manner by applying the polymeric solution and allowing the solvent to evaporate. Preferably, the electrochemical cell is stored in a buffered solution if it is not going to be used immediately for measuring the oxygen concentration of the fluid.

The foregoing has described the improved cathode of the present invention along with the improved electrochemical cell utilizing the cathode of the present invention.

We claim:

1. In a sensing device for measuring $PO_2$ in a fluid, the improvement comprising an electrode assembly for $PO_2$, wherein the electrode assembly is part of a printed wiring board and wherein the electrode assembly, comprises:

a nonconducting substrate, at least one thick film metallic layer overlying the said nonconducting substrate in a pattern to provide distinct cathode and anode and conductive pathways to both electrodes where the pathways are electrically isolated from each other and where each is capable of eventual external electrical connection from the electrode assembly and where the anode has a semi-circular shape for uniform current density between the anode and cathode electrodes, an encapsulant layer overlying that portion of said metallic layer other than the anode to electrically isolate the conductive pathway to the anode from the conductive pathway to the cathode in the metallic layer and having at least one laser-produced finite-sided opening with a bottom, where at least a portion of the walls of said opening are formed by the encapsulant layer, and where the opening exposes in addition to the portion of the walls of the opening that is comprised of the encapsulant layer, the remaining portion of the walls that is comprised of the metallic layer, and wherein the bottom of the opening is comprised of the metallic layer, so that the metallic portion of the walls and of the bottom act as the cathode, and where the opening is capable of ionic contact and where the cathode has a diameter between 0.001 and 0.0015±0.0003 inches, and where the ratio of the surface area of the anode to the surface area of the cathode is between 50 to 1 and 300 to 1; and an electrolyte present in the electrode assembly to provide ionic contact with the cathode and the adjacent anode for electrical ionic relationship between the cathode and anode.

2. The sensing device of claim 1 wherein the anode with the semi-circular shape is equidistant from the cathode opening at every point along the semicircle.

3. The sensing device of claim 1 wherein the electrolyte is selected from the group consisting of a gel and liquid and when a liquid there is a membrane covering the electrolyte.

4. The sensing device of claim 1 wherein cathode and anode are placed in the electrode assembly to have a distance from the center of the cathode to the edge of the anode in the range of around 0.013 to 0.015 of an inch.

5. In a sensing device for measuring $PO_2$ in a fluid, the improvement comprising an electrode assembly for $PO_2$, wherein the electrode assembly is part of a printed wiring board and wherein the electrode assembly, comprises:

a nonconducting substrate, at least one thick film metallic layer overlying the said nonconducting substrate in a pattern to provide distinct cathode and anode and conductive pathways to both electrodes where the pathways are electrically isolated from each other and where each is capable of eventual external electrical connection from the electrode assembly and where the anode has a semi-circular shape for uniform current density between the anode and cathode electrodes, an encapsulant layer overlying that portion of said metallic layer other than the anode to electrically isolate the conductive pathway to the anode from the conductive pathway to the cathode in the metallic layer and having at least one laser-produced finite-sided opening with a bottom, where at least a portion of the walls of said opening are formed by the encapsulant layer, and where the opening exposes in addition to the portion of the walls comprised of the encapsulant layer, the remaining portion of the walls comprised of the metallic layer, and wherein the bottom of the opening is at the nonconducting base so that the metallic portion of the walls forms an annular metallic portion of the walls that acts as the cathode, and where the opening is capable of ionic contact and where the cathode has a diameter between 0.001 and 0.0015±0.0003 inches, and where the ratio of the surface area of the anode to the surface area of the cathode is between 50 to 1 and 300 to 1; and an electrolyte present in the electrode assembly to provide ionic contact with the cathode and the adjacent anode for electrical ionic relationship between the cathode and anode.

6. The sensing device of claim 5 wherein the anode with the semi-circular shape is equidistant from the cathode opening at every point along the semicircle.

7. The sensing device of claim 5 wherein the electrolyte is selected from the group consisting of a gel and liquid and when a liquid there is a membrane covering the electrolyte.

8. The sensing device of claim 5 wherein cathode and anode are placed in the electrode assembly to have a distance from the center of the cathode to the edge of the anode in the range of around 0.013 to 0.015 of an inch.

* * * * *